United States Patent [19]

Jung et al.

[11] Patent Number: 5,075,477

[45] Date of Patent: Dec. 24, 1991

[54] DIRECT SYNTHESIS OF METHYLCHLOROSILAAKANES

[75] Inventors: Il Nam Jung; Gyu-Hwan Lee; Seung Ho Yeon; Mi-Yeon Suk, all of Seoul, Rep. of Korea

[73] Assignee: Korea Institute of Science and Technology, Rep. of Korea

[21] Appl. No.: 697,165

[22] Filed: May 8, 1991

[30] Foreign Application Priority Data

Jan. 22, 1991 [KR] Rep. of Korea ............... 1055/1991

[51] Int. Cl.$^5$ ............................................. C07F 7/08
[52] U.S. Cl. .................................................. 556/435
[58] Field of Search ........................................ 556/435

[56] References Cited

U.S. PATENT DOCUMENTS

| | | | |
|---|---|---|---|
| 2,507,513 | 5/1950 | Goodwin | 556/535 |
| 3,527,781 | 9/1970 | Levin | 556/435 X |
| 4,278,908 | 10/1988 | Pillot et al. | 556/435 |
| 5,026,893 | 6/1991 | Pacioreh et al. | 556/435 |

*Primary Examiner*—Paul F. Shaver
*Attorney, Agent, or Firm*—Townsend and Townsend

[57] ABSTRACT

A novel and improved method for simultaneously producing 2,4,6-trisilaheptane of the following formula (I) and 1,3-disilabutane of the following formula (II), which are the starting material essential for forming silicon polymers: wherein, R is methyl group or chloro group.

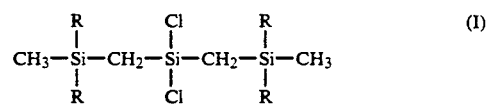

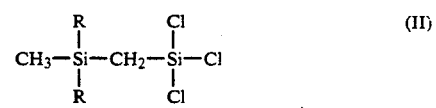

The method is characterized by reacting silicon and chloromethylsilanes of the following formula (III) at 250° C.–350° C. and in the presence of copper as a catalyst, exclusively or together with cadmium powder as a co-catalyst.

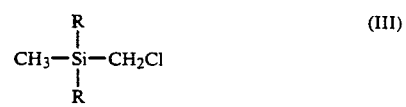

4 Claims, No Drawings

DIRECT SYNTHESIS OF METHYLCHLOROSILAAKANES

FIELD OF THE INVENTION

The present invention relates to a method for preparing methylchlorosilaalkanes by directly reacting α-chloromethylsilanes represented in formula III with silicon metal to give trisilaalkane compounds having dichlorosilyl group at the middle of the structure in formula as the major products and disilaalkane compounds having trichlorosilyl group at the end of the structure in formula II in moderately high yields in the present of copper catalyst at a temperature from 250° C. to 350° C. The preferred reaction temperature range is 300°–330° C. Useful copper catalysts include copper metal, copper salts, and partially oxidized copper.

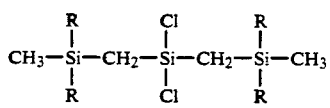   (I)

In formula I, R represents methyl or chloride.

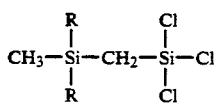   (II)

In formula II, R represents methyl or chloride.

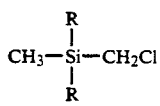   (III)

In formula III, R represents methyl or chloride.

DESCRIPTION OF THE PRIOR ART

Methylchlorosilanes are the most important starting materials for silicones. E. G. Rochow discovered the direct process for the synthesis of methylchlorosilanes, reacting elemental silicon with methylchloride in the present of a catalyst in 1940 (E. G. Rochow U.S. Pat. No. 2,380,995).

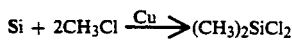

The reaction gives dimethyldichlorosilane, methyltrichlorosilane, trimethylchlorosilane, and tetrachlorosilane. A number of high boiling compounds are also found in the mixture of the products in a small quantity. The reaction rate and the nature of products depend on a large number of factors. These determining factors include the nature of the starting materials, the catalyst, the reaction temperature, the reaction pressure, the type of reactor used, and the degree of conversion of silicon and methylchloride.

The catalyst for the direct process is always copper, in some cases co-catalysts such as zinc, aluminum, cadmium etc. are added. The co-catalysts enhance the reactivity of silicon metal and shorten the induction period and increase the selectivity of dimethyldichlorosilane production. The reactions is carried out at 250°–350° C., and the yield of dimethyldichlorosilane decreases at temperatures above 300° C. In the absence of the catalyst, the reaction is sluggish and gives irreproducible results (E. G. Rochow, J. Am. Chem. Soc., 67,963 (1945)). The composition of the products depends on the amount of copper used. The greater amount of copper is used, the higher is the chlorine content of the resulting products. The greatest catalytic efficiency is obtained when the amount of copper is 10% of the amount of silicon.

The reactivity of the Silicon-Copper mixture is connected with the formation of an intermetallic η-phase ($Cu_3Si$). The present of the η-phase in the mixture is of fundamental importance for the selective synthesis of dimethyldichlorosilane. It is known that the mixture of silicon powder and copper powder is heated 800° to 1000° C. in nitrogen, or better in hydrogen, the powders become sintered and the η-phase is formed (P. Trambouze and B. Imelik, J. Chim. Phys., 51,505 (1954)). The η-phase is also chemically prepared by heating cuprous chloride with silicon at the temperature above 350° C. (E. G. Rochow in Inorganic synthesis, III. Mc Graw-Hill, New York 1950, p56).

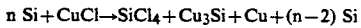

The reaction rate and the composition of the products in the direct process are highly temperature-dependent (A. L. Klebamskii and V. S. Fikhtengolts, J. Gen. Chem. U.S.S.R., 27, 2693 (1957)). It is much important to maintain the reaction temperature at an accurately specified temperature and to prevent any hot spot developing in the agglomerates of the solid phase. It is reported that at higher temperatures, the deposition of carbon on the surface of the metal mixture occur which slows down the reaction (J. C. Vlugter and R. J. H. Voorhoeve, Conf. Accad. Lincei, Alta Tech. Chim. 1961 p81 (1962)). This is why the reactor for the direct synthesis of methylchlorosilane must have a high thermal stability and an efficient heat transfer.

The direct process can be carried out in fixed bed, in stirred bed, and also in fluidized bed reactors. The process with the stirred bed reactors has the advantages over the fixed bed operation that the heat of reaction can be removed more efficiently and the movement of the powders causes fresh surface to be continuously exposed (H. Grohm and R. Pau dert, Chem. Techn. 10, 307 (1958)). Sellers and Davis reported that a mechanically stirred fluidized bed could be used (J. E. Sellers and J. L. Davis, U.S. Pat. No. 2,449,821). The metal powder was agitated in an up and down motion in a vertical reactor by means of spiral band rotated by a central shaft while a stream of methylchloride was flowing upward through metal powder. Bluestrim used a fluidized bed reactor for the production of methylchlorosilane (B. A. Bluestrm, U.S. Pat. No. 2,887,502). Dotson further improved the fluidized-bed process by continuously or intermittently removing a portion of the solid powder from the reactor space and grinding it in a jet mill before returning it to the reactor (J. M. Dotson, French Pat. 1,311,472).

Patnode and Schiesster reported that linear and cyclic silaalkanes could be prepared by reacting silicon with methylene chloride in the present of copper in the fluidized bed reactor (W. I. Patnode and R. W. Schiessler, U.S. Pat. Nos. 2,381,000, 2,381,001 and 2,381,002).

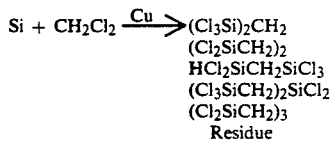

Muller and Seitz also reported that chlorosilaalkanes could be prepared by the reaction of silicon with chloroform. This reaction was carried out at about 320° C. in a fluidized bed to give branched and cyclic chlorosilaalkanes (R. Muller and G. Seitz., Chem. Ber. 91, 22 (1958)).

Muller and coworkers also reported the reaction of silicon with carbon tetrachloride. The reaction gave chlorosilyl substituted methanes, ethylenes and acetylenes (K. Muller and H. Beyer, Chem. Ber., 92, 1018 (1959)). The formation of various products in low yields from the reactions between silicon and polychlorinated methanes such as $CH_2Cl_2$, $CHCl_3$ and $CCl_4$ suggest that the reactions proceed via a variety of routes, such as dechlorination and dehydrochlorination. The decomposition of chlorinated methanes gives carbon deposition on the surface of metal, which leads to deactivation of metal.

Mironov et al reported the preparations of chlorosilaalkanes by reacting silicon metal with α-chloromethylsilanes. The reaction of α-chloromethylsilanes with silicon metal is very similar to that of methylchloride with silicon and gives the products having dichlorosilyl group at the middle of the structure of trichlorosilyl group at the end. 1,1,1,3,3-pentachloro-1,3-disilabutane and 2,2,4,4,6,6-hexachloro-2,4,6-trisilaheptane were obtained from the reaction of chloromethylmethyldichlorosilane with silicon at the reaction temperature between 360°-370° C. in 28.7% and 16.7% yields respectively (A. D. Petrov, S. I. Sahykh-Zade, E. A. Chernyshev, V. F. Mironov, Zh. Obschch. Khim., 26, 1248 (1956). α-Chloromethylsilanes are known to be easily prepared by the chlorination of corresponding methylsilanes under UV irradiation in refluxing carbon tetrachloride (R. H. Krieble and J. R. Elliott, J. Am. Chem. Soc., 67, 1810 (1945)).

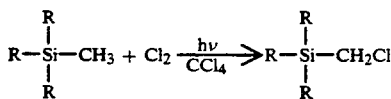

where R may independently be Cl or methyl.

When chloromethyldimethylchlorosilane was reacted with silicon at 370°-390° C., only a small amount of 3-methyl-1,1,1,3-tetrachloro-1,3-disilabutane and 2,6-dimethyl-2,4,4,6-tetrachloro-2,4,6-trisilaheptane were obtained (V. F. Mironov, T. K. Gar, A. A. Buyaknov, Zh. Obshch. Khim., 42, 1361 (1972)). They also claimed that the yields of the reaction between α-chloromethylsilanes and silicon metal in the presence of copper catalyst were improved by adding zinc and cadmium as promoters at 400°-500° C. (V. F. Mironov, T. K. Gar, V. D. Sheludyakov, A. A. Buyakov, V. I. Andreev. I. N. Petrova, U.S.S.R. Patent 394,378). In all cases above the yields were not very high and the major products were trichlorosilyl group terminated disilaalkane compounds. This indicated that the dechlorination or decomposition of the starting silane was involved. The decomposition of the starting material or the products made the process economically less feasible and easily deactivated the silicon metal.

SUMMARY OF THE INVENTION

The present invention relates to a method for preparing methylchloro-silaalkanes by reacting α-chloromethylsilanes represented in formula III with silicon metal to give the trisilaalkane compounds having dichlorosilyl group at the middle of the structure in formula I as the major products and the disilaalkane compounds having trichlorosilyl group at the end in formula II in moderately high yields in the present of copper catalyst at a temperature from 250° C. to 350° C. The preferred reaction temperature range is 300°-330° C. Useful copper catalysts include copper metal, copper salts, and partially oxidized copper. The reaction can be carried out in a fluidized bed or in a stirred bed reactor. In the fluidized bed reaction, a good fluidization of the powders is not easily obtained due to high boiling points and high viscosities of the starting materials and the products. The addition of inert nitrogen gas to the starting reactant vapor is recommended to improve the fluidization. This also helps to remove the high boiling products out of the reactor. Addition of micro-spherical acid clay to silicon metal improved the fluidization and gave better results.

The commercially available copper catalysts for the reaction between silicon and methyl chloride are also found to be good catalysts for these reactions. The process in this invention is characterized to exclude zinc or cadmium promotors which have been claimed previously by Mironov et al (U.S.S.R. Patent 394,378). Zinc is found to be an inhibitor rather than promotor in this invention.

The reaction in the stirred reactor equipped with a spiral band agitator gives the comparable results with those obtained using the fluidized bed reactor. The reactant can be passed from the bottom to the top or the reverse direction. In either cases, some addition of inert gases such as nitrogen or argon to the starting material is advised. When the starting silane is blown from the top to bottom, better results are obtained probably due to easier removal of high boiling by-products with-out vaporizing them. If the high boiling by-products stay in the reactor, they may eventually decompose and give carbon deposition which will cause the metal deactivation. One of the advantages of this reaction is that fine silicon powders which may not be used for the fluidized reaction can be used.

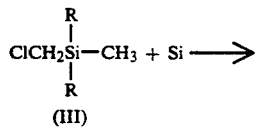

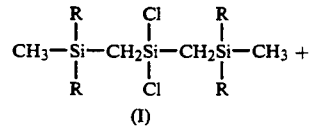

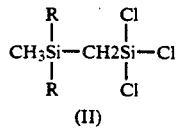

The commercially available copper catalysts for the reaction between silicon and methylchloride are also good for the reactions in the present invention. The reaction using cuprous chloride as the catalyst gives comparable results. Zinc and Cadmium powders are known to be co-catalysts for the reactions but zinc is found to be an inhibitor for the reactions and cadmium is found to be a good promotor in the invention.

The compositions of the products at various reaction conditions are shown in Table 1. The results shown in the Table 1 are obtained from the reactions in which reactants were introduced from the top of the agitator type reactor, and products were collected from the bottom unless stated otherwise. The Table 1 contains the results of Examples 1 to 13.

TABLE 1

| | | | | | | Composition ratio of products (%) | | | | |
|---|---|---|---|---|---|---|---|---|---|---|
| | Silane of General formula (III) | | | | | | | | | |
| Example Nos. | R | used amount (g) | Catalyst/ co-catalyst | Reaction time hrs. | Amount of products (g) | compounds of General formula (I) | Compounds of General formula (II) | others | Starting materials, Compounds of General formula (III) | reference column |
| 1 | Me Cl | 189.6 | CuCl | 18.5 | 198.6 | 54.2 | 12.7 | 33.1 | 0.0 | |
| 2 | Me Cl | 366.8 | Cu | 37 | 387.2 | 51.2 | 9.0 | 8.9 | 30.9 | |
| 3 | Me Cl | 49.4 | Cu/Zn | 5 | 49.2 | — | 7.8 | 30.1 | 62.1 | |
| 4 | Me Cl | 45.5 | Cu/Cd | 4.5 | 46.8 | 80.8 | 2.5 | 16.7 | 0.0 | |
| 5 | Me Cl | 135.6 | Cu/Cd | 7 | 135.3 | 54.4 | 2.1 | 7.6 | 35.9 | Fluidized bed-type reaction bath |
| 6 | Cl Cl | 135.1 | CuCl | 14 | 136.9 | 34.2 | 28.3 | 22.1 | 15.4 | |
| 7 | Cl Cl | 62.7 | Cu | 6 | 64.7 | 46.3 | 8.3 | 9.4 | 36.0 | |
| 8 | Cl Cl | 139.4 | Cu/Cd | 13 | 144.7 | 60.5 | 19.1 | 20.4 | 0.0 | |
| 9 | Me Me | 146.6 | CuCl | 18 | 148.1 | 11.8 | 8.9 | 27.1 | 52.2 | |
| 10 | Me Me | 61.7 | Cu | 6 | 63.0 | 28.5 | 0.4 | 1.1 | 70.0 | |
| 11 | Me Me | 65.6 | Cu/Cd | 8 | 66.8 | 87.5 | 6.5 | 6.0 | 0.0 | Acid clay |
| 12 | Me Me | 40.2 | Cu/Cd | 5 | 41.6 | 83.2 | 6.8 | 6.4 | 1.7 | |
| 13 | Me Cl | 108.5 | Cu/Cd | 10.5 | 113.8 | 82.2 | 2.3 | 15.5 | 0.0 | Acid clay |

Preparations of Si/Cu contact mixture being used in the method according to the present invention are as follows.

Si/Cu contact mixture:

After about 99 g (325–60 mesh) of silicon is mixed with 17.3 g of CuCl (10% of copper based on the weight of the silicon and copper) as a catalyst in order to provide a mixture, the mixture is contained in the reactor. Thereafter, the mixture was heated to a temperature ranging from 180° C. to 200° C. At this time, the agitator rotates at 60 rpm. in order to mix the mixture completely together with blowing slowly dried nitrogen. When the temperature in the reactor is raised to about 370° C., the silicon reacts with the CuCl to form $\eta$-phase $Cu_3Si$, and $SiCl_4$ is obtained as a by-product which is removed from the reactor.

In case of using copper catalysts which were used in the synthesis of methylchlorosilanes instead of the CuCl, 10% of the copper based on the weight of the silicon and copper was mixed with the silicon. The mixture was heated temperature of 350° C. for 2 hours in the reactor together with blowing hydrogen or methylchloride in order to be activated.

The present invention will be further described by the following nonlimiting examples.

EXAMPLE 1

Reaction of silicon and chloromethyldimethylchlorosilane 100 g of Si/Cu contact mixture obtained from silicon and CuCl was charged in an agitating-type reaction bath. After increasing the temperature in the reactor up to 320° C., 189 g of chloromethyl dimethylchlorosilane was charged in a dropping funnel. Thereafter, silane was dropped from the funnel, while $N_2$ was also blown therein at the rate of 60 ml/min. 5 minutes after the initiation of dropping, increase of the temperature caused by an exothermic nature of the reaction was observed and reaction product of high viscosity began to flow along the wall of an receiver flask. While maintaining the above conditions, reaction product was taken every hour.

The obtained reaction products were analyzed by using a gas chromatography (capillary column, SE-54, 12 m, or Packed column, SE-30, 4.25 m×⅛" OD. SS) and fractionally distilled to separate its constituents from one another, so that their structures could be determined. A part of reaction product was treated with lithium aluminum hydride in order to reduce Si-Cl to Si-H entirely, and then its structure was determined by using an infrared spectroscopy, a nuclear magnetic resonance spectroscopy and a mass spectroscopy.

After the reaction for 18.5 hours, 198.6 g of product was obtained, the composition of which contains 107.6 g (54.2%) of 2,4,4,6-tetrachloro-2,6-dimethyl-2,4,6-trisilaheptane [bp 94°–95° C. (1.5 torr); NMR (CCl₄) 0.66 ppm (s, 12H, CH₃), 1.05 ppm (s, 4H, CH₂)] and 25.2 g (12.7%) of 1,1,1,3-tetrachloro-3-methyl-1,3-disilabutane [bp 169.5°–170° C.; NMR 0.66 ppm (s, 6H, CH₃), 1.30 ppm (s, 2H, CH₂). 33.1% of by-product contained 13% of trimethylchlorosilane and about 20% of the balance was unidentified substances.

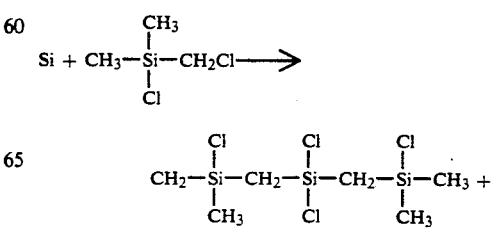

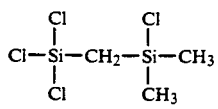

EXAMPLE 2

Reaction of silicon and chloromethyldimethylchlorosilane

The reaction was carried out under the same condition and by the same reactor as employed in Example 1, except that Si/Cu contact mixture obtained from silicon and copper was used. After the reaction for 37 hours, 387.2 g of product was obtained, the composition of which was determined by the gas chromatography to contain 51.2% of 2,4,4,6-tetrachloro-2,6-dimethyl-2,4,6-trisilaheptane and 9.0% of 1,1,1,3-tetrachloro-3-methyl-1,3-disilabutane. Other by-product contained was 8.9% of trimethylchlorosilane and 30.9% of the balance was the starting material.

EXAMPLE 3

Reaction of silicon and chloromethyldimethylchlorosilane

The reaction was carried out under the same condition and by the same reactor as employed in Example 2, except that 0.5% of zinc powder as co-catalyst was added thereto. After the reaction for 5 hours, 49.2 g of product was obtained, the composition of which contained almost no 2,4,4,6-tetrachloro-2,6-dimethyl-2,4,6-trisilaheptane and 7.8% of 1,1,1,3-tetrachloro-3-methyl-1,3-disilabutane. 30.1% of by-product contained 8.9% of trimethylchlorosilane. 62.1% of starting material as the balance was recovered.

EXAMPLE 4

Reaction of silicon and chloromethyldimethylchlorosilane

The reaction was carried out under the same condition and by the same reactor as employed in Example 3, except that in place of zinc powder, 0.5% of cadmium was used as the co-catalyst added to Si/Cu contact mixture obtained from silicon and copper. After the reaction for 4.5 hours, 46.8 g of product was obtained, the composition of which was determined by the gas chromatography to contain 40.2 g (80.8%) of 2,4,4,6-tetrachloro-2,6-dimethyl-2,4,6-trisilaheptane and 1.2 g (2.5%) of 1,1,1,3-tetrachloro-3-methyl-1,3-disilabutane. 8.2 g (16.7%) of by-product contained 9.1% of trimethylchlorosilane. No starting material was recovered.

EXAMPLE 5

Reaction of silicon and chloromethyldimethylchlorosilane

The reaction was carried out under the same condition and by the same reactor as employed in Example 4, except that a fluidized bed-type reaction bath was used, in place of the agitating-type bath, and that 15 g of fine powder-type acid clay was added to 300 g of Si/Cu contact mixture. The reactant was fluidized by nitrogen and silane reactant was added. After the reaction for 7 hours, 135.3 g of product was obtained, the composition of which contained 54.4% of 2,4,4,6-tetrachloro-2,6-dimethyl-2,4,6-trisilaheptane and 2.1% of 1,1,1,3-tetrachloro-3-methyl-1,3-disilabutane. 35.9% of starting material was recovered.

EXAMPLE 6

Reaction of silicon and chloromethylmethyldichlorosilane

The reaction was carried out under the same condition and by the same reactor as employed in Example 1, except that chloromethyl methyldichlorosilane was used, in place of chloromethyl dimethylchlorosilane. After the reaction for 14 hours, 136.9 g of product was obtained, the composition of which contained 46.8 g (34.2%) of 2,2,4,4,6,6-hexachloro-2,4,6-trisilaheptane [bp 97°–97.5° C. (1.5 torr); NMR (CCl$_4$) 0.91 ppm (s, 6H, CH$_3$), 1.33 ppm (s, 4H, CH$_2$)] and about 38.7 g (28.3%) of 1,1,1,3,3-pentachloro-1,3-disilabutane [bp 181.5°–182° C.; NMR 0.92 ppm (s, 3H, CH$_3$), 1.53 ppm (s, 2H, CH$_2$). The greater part of 30.2 g (22.1%) of by-product was dimethyldichlorosilane. 15.4% of starting material was recovered.

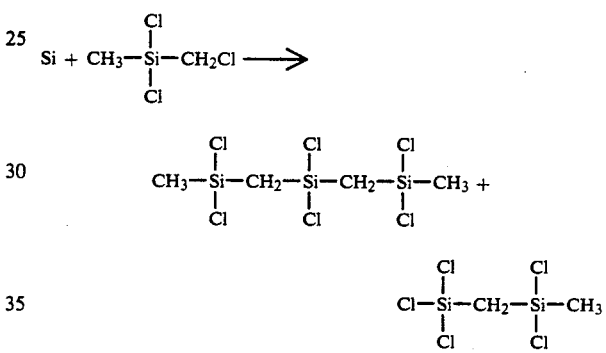

EXAMPLE 7

Reaction of silicon and chloromethylmethyldichlorosilane

The reaction was carried out under the same condition and by the same reactor as employed in Example 2, except that chloromethyl methyldichlorosilane was used, in place of chloromethyl dimethylchlorosilane. After the reaction for 6 hours, 64.7 g of product was obtained, the composition of which contained 30.0 g (46.3%) of 2,2,4,4,6,6-hexachloro-2,4,6-trisilaheptane and 5.4 g (8.3%) of 1,1,1,3,3-pentachloro-1,3-disilabutane. 36.0% of starting material was recovered. 9.4% of by-product contained 4% of dimethyldichlorosilane.

EXAMPLE 8

Reaction of silicon and chloromethylmethyldichlorosilane

The reaction was carried out under the same condition as employed in Example 4, except that chloromethylmethyldichlorosilane was used, in place of chloromethyldimethylchlorosilane. After the reaction for 13 hours, 144.7 g of product was obtained, the composition of which contained 87.7 g (60.5%) of 2,2,4,4,6,6-hexachloro-2,4,6-trisilaheptane and 27.6 g (19.1%) of 1,1,1,3,3-pentachloro-1,3-disilabutane. 20.4% of by-product contained 8.0% of dimethyl dichlorosilane. No starting material was recovered.

EXAMPLE 9

Reaction of silicon and chloromethyltrimethylsilane

The reaction was carried out under the same condition and by the same reactor as employed in Example 1, except that chloromethyltrimethylsilane was used, in place of chloromethyldimethylchlorosilane. After the reaction for 18 hours, 148.1 g of product was obtained, the composition of which contained 17.5 g (11.8%) of 2,2,6,6-tetramethyl-4,4-dichloro-2,4,6-trisilaheptane [bp 112°–115° C. (9 torr); NMR (CCl$_4$) 0.55 ppm (s, 4H, —CH$_2$), 0.20 ppm (s, 18H, CH$_3$)] and 13.2 g (8.9%) of 1,1,1-trichloro-3,3-dimethyl-1,3-disilabutane [bp 173°–174° C.; NMR (CCl$_4$) 0.25 ppm (s, 9H, CH$_3$), 0.85 ppm (s, 2H, CH$_2$). 27.1% of by-product contained 16.8% of tetramethylsilane. 52.2% of starting material was recovered.

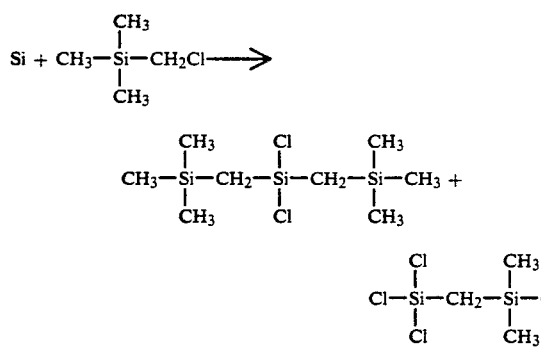

EXAMPLE 10

Reaction of silicon and chloromethyltrimethylsilane

The reaction was carried out under the same condition as employed in Example 2, except that 11 g of Cu powder was used as catalyst, in place of CuCl. After the reaction for 6 hours, 63.0 g of product was obtained, the composition of which contained 16.5 g (28.5%) of 2,2,6,6-tetramethyl-4,4-dichloro-2,4,6-trisilaheptane and 0.4% of 1,1,1-trichloro-3,3-dimethyl-1,3-disilabutane. 1.1% of by-product was tetramethylsilane. 70% of starting material was recovered.

EXAMPLE 11

Reaction of silicon and chloromethyltrimethylsilane

The reaction was carried out under the same condition as employed in Example 4, except that 11 g of Cu powder was used as catalyst, in place of CuCl. 0.6 g of cadmium powder was also used as co-catalyst. After the reaction for 8 hours, 66.8 g of product was obtained, the composition of which contained 58.5 g (87.5%) of 2,2,6,6-tetramethyl-4,4-dichloro-2,4,6-trisilaheptane and 4.3 g (6.5%) of 1,1,1-trichloro-3,3-dimethyl-1,3-disilabutane. The greater part of about 6.0% by-product was tetramethylsilane. No starting material was recovered.

EXAMPLE 12

Reaction of silicon and chloromethyltrimethylsilane

The reaction was carried out under the same condition as employed in Example 4, except that silane was injected from the bottom of the reactor and product was taken from the top of the reactor. After the reaction for 5 hours, 41.6 g of product was obtained, the composition of which contained 34.6 g (83.2%) of 2,2,6,6-tetramethyl-4,4-dichloro-2,4,6-trisilaheptane and 2.8 g (6.8%) of 1,1,1-trichloro-3,3-dimethyl-1,3-disilabutane. 6.4% of by-product was formed, and 1.7% of starting material was recovered.

EXAMPLE 13

Reaction of silicon and chloromethyldimethylchlorosilane

The reaction was carried out under the same condition and by the same reactor as employed in Example 4, except that about 5 g of spherical fine powder-type acid clay was added to Si/Cu contact mixture. As a result, stirring could be much easier. After the reaction for 10.5 hours, 113.8 g of product was obtained, the composition of which contained 82.2% of 2,4,4,6-tetrachloro-2,6-dimethyl-2,4,6-trisilaheptane and 2.3% of 1,1,1,3-tetrachloro-3-methyl-1,3-disilabutane. No starting material was recovered.

EXAMPLE 14

Reaction of silicon and chloromethyldimethylchlorosilane

The reaction was carried out under the same condition and by the same reactor as employed in Example 4, except that 0.6 g of cadmium and 0.6 g of zinc powder were used as co-catalyst. After the reaction for 4 hours, 40.5 g of product was obtained, the composition of which contained 6.3 g (15.5%) of 1,3,3,5-tetrachloro-3,5-dimethyl-2,4,6-trisilaheptane and 14.5 g (35.8%) of 1,1,1,3-tetrachloro-3-methyl-1,3-disilabutane. 48.7 g of by-product contained about 7.8% of trimethylchlorosilane and 5.6% of dimethyldichlorosilane. 1.7% of starting material was recovered.

EXAMPLE 15

Reaction of silicon and chloromethyldimethylchlorosilane

The reaction was carried out under the same condition and by the same reactor as employed in Example 1, except that the reaction temperature was raised up to 340° C. After the reaction for 13 hours, 139.6 g of product was obtained, the composition of which contained 20.1% of 2,4,4,6-tetrachloro-2,6-dimethyl-2,4,6-trisilaheptane and 15.2% of 1,1,1,3-tetrachloro-3-methyl-1,3-disilabutane. 35.7% of starting material was recovered.

EXAMPLE 16

Reaction of silicon and chloromethyldimethylchlorosilane

The reaction was carried out under the same condition and by the same reactor as employed in Example 15, except that the reaction temperature was lowered to 300° C. After the reaction for 12 hours, 129.4 g of product was obtained, the composition of which contained 32.7% of 2,4,4,6-tetrachloro-2,6-dimethyl-2,4,6-trisilaheptane and 19.2% of 1,1,1,3-tetrachloro-3-methyl-1,3-disilabutane. 22.8% of starting material was recovered.

EXAMPLE 17

Reaction of silicon and chloromethyldimethylchlorosilane

The reaction was carried out under the same condition and by the same reactor as employed in Example 15, except that the reaction temperature was 280° C.

After the reaction for 13 hours, 145.7 g of product was obtained, the composition of which contained 32.7% of 2,4,4,6-tetrachloro-2,6-dimethyl-2,4,6-trisilaheptane and 26.6% of 1,1,1,3-tetrachloro-3-methyl-1,3-disilabutane. 12.6% of starting material was recovered.

What is claimed is:

1. In a method for producing 2,4,6-trisilaheptanes of the following general formula (I) and 1,3-disilabutane of the following general formula (II), the improvement comprising reacting silicon and chloromethylsilane of the following formula (III) at 250° C.–350° C. and in the presence of a catalyst, exclusively or together with a co-catalyst:

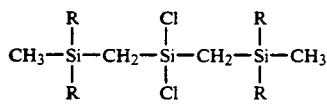 (I)

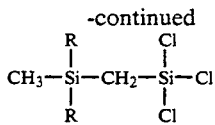 (II)

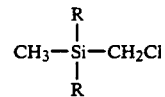 (III)

in the general formula (I), R is methyl group or chloro group; in the general formula (II), R is methyl group or chloro group; and in the general formula (III), R is methyl group or chloro group.

2. The method in accordance with claim 1, wherein about 10%–15% of copper or cuprous chloride based on the amount of all reactants is used as the catalyst.

3. The method in accordance with claim 1, wherein about 0.1%–5% of cadmium powder based on the amount of all reactants is used as the co-catalyst.

4. The method in accordance with claim 1, wherein in the reaction, about 5%–10% of micro-spherical acid clay based on the amount of silicon is added.

* * * * *